(12) United States Patent
Helmer et al.

(10) Patent No.: US 12,171,990 B2
(45) Date of Patent: Dec. 24, 2024

(54) SENSOR DEVICE FOR ATTACHMENT TO AN INJECTION DEVICE

(71) Applicant: SANOFI, Paris (FR)

(72) Inventors: Michael Helmer, Frankfurt am Main (DE); Christian Rehbein, Nieder-Olm (DE)

(73) Assignee: SANOFI, Paris (FR)

( * ) Notice: Subject to any disclaimer, the term of this patent is extended or adjusted under 35 U.S.C. 154(b) by 811 days.

(21) Appl. No.: 16/957,329

(22) PCT Filed: Dec. 20, 2018

(86) PCT No.: PCT/EP2018/086099
§ 371 (c)(1),
(2) Date: Jun. 23, 2020

(87) PCT Pub. No.: WO2019/129618
PCT Pub. Date: Jul. 4, 2019

(65) Prior Publication Data
US 2020/0368442 A1 Nov. 26, 2020

(30) Foreign Application Priority Data

Dec. 28, 2017 (EP) .................................. 17306951

(51) Int. Cl.
*A61M 5/315* (2006.01)
*A61M 5/31* (2006.01)
(Continued)

(52) U.S. Cl.
CPC ........... *A61M 5/3157* (2013.01); *G01D 5/145* (2013.01); *G01D 5/16* (2013.01); *G01D 5/2013* (2013.01);
(Continued)

(58) Field of Classification Search
CPC ........ G01D 5/145; G01D 5/16; G01D 5/2013; G01H 11/08; A61M 2205/3317; A61M 5/3157
See application file for complete search history.

(56) References Cited

U.S. PATENT DOCUMENTS 6,620,133 B1 * 9/2003 Steck ...................... A61M 5/20
604/67
9,526,838 B2 * 12/2016 Baran ....................... F16B 2/20
(Continued)

FOREIGN PATENT DOCUMENTS

| CN | 101014378 | 8/2007 |
|---|---|---|
| CN | 104066467 | 9/2014 |

(Continued)

OTHER PUBLICATIONS

PCT International Preliminary Report on Patentability in International Appln. No. PCT/EP2018/086099, dated Jun. 30, 2020, 10 pages.
(Continued)

*Primary Examiner* — Jason E Flick
*Assistant Examiner* — Adam J. Cermak
(74) *Attorney, Agent, or Firm* — Bond, Schoeneck & King, PLLC

(57) ABSTRACT

A supplementary device is configured to be releasably attached to an auto injector type device. The supplementary device is suitable for use with disposable one-shot auto injectors and re-usable one-shot auto injectors. The supplementary device has at least one inductive proximity sensor which outputs signals indicative of the position moveable components within the auto injector. The supplementary device is configured to determine based on the outputted signals the moment at which the auto injector changes from a pre-ejection state to a post-ejection state. In response to determining that the auto injector has changed from the
(Continued)

pre-ejection state to the post ejection state, the supplementary device displays a visual indication that a user should hold the auto injector in its current position for a predetermined period of time.

10 Claims, 14 Drawing Sheets

(51) Int. Cl.
  *G01D 5/14* (2006.01)
  *G01D 5/16* (2006.01)
  *G01D 5/20* (2006.01)
  *G01H 11/08* (2006.01)

(52) U.S. Cl.
  CPC ..... *G01H 11/08* (2013.01); *A61M 2005/3126* (2013.01); *A61M 2205/0272* (2013.01); *A61M 2205/18* (2013.01); *A61M 2205/3317* (2013.01); *A61M 2205/3584* (2013.01); *A61M 2205/52* (2013.01); *A61M 2205/581* (2013.01); *A61M 2205/583* (2013.01); *A61M 2205/587* (2013.01)

(56) References Cited

U.S. PATENT DOCUMENTS

| | | | | |
|---|---|---|---|---|
| 10,195,355 | B2* | 2/2019 | Allerdings | A61M 5/31535 |
| 2003/0114801 | A1* | 6/2003 | Woolston | A61M 5/14566 604/245 |
| 2010/0145656 | A1* | 6/2010 | Koehler | G16H 20/17 702/182 |
| 2011/0208125 | A1* | 8/2011 | Larsen | A61M 5/24 604/189 |
| 2011/0313349 | A1* | 12/2011 | Krulevitch | A61M 5/315 604/65 |
| 2012/0233834 | A1 | 9/2012 | Szechinski et al. | |
| 2014/0058349 | A1* | 2/2014 | Bazargan | A61M 5/14212 604/93.01 |
| 2014/0142537 | A1* | 5/2014 | Gibson | A61M 5/14546 604/67 |
| 2014/0221913 | A1* | 8/2014 | Banister | A61M 5/1723 604/150 |
| 2014/0243750 | A1* | 8/2014 | Larsen | A61M 5/24 604/218 |
| 2014/0296787 | A1* | 10/2014 | Agard | A61M 5/172 604/152 |
| 2014/0331996 | A1 | 11/2014 | Elmen | |
| 2014/0354998 | A1* | 12/2014 | Bock | G01J 1/08 356/445 |
| 2015/0018770 | A1* | 1/2015 | Baran | F16B 21/088 403/321 |
| 2015/0025470 | A1* | 1/2015 | Baran | A61B 5/4839 604/187 |
| 2015/0032059 | A1* | 1/2015 | Allerdings | G16H 40/63 604/189 |
| 2016/0015910 | A1* | 1/2016 | Mukai | A61M 5/5086 604/111 |
| 2016/0030683 | A1* | 2/2016 | Taylor | A61M 5/345 604/151 |
| 2016/0045674 | A1* | 2/2016 | Blei | G01N 21/553 604/207 |
| 2016/0074587 | A1* | 3/2016 | Searle | A61M 5/16831 604/189 |
| 2016/0082192 | A1* | 3/2016 | Veasey | G16H 40/63 604/211 |
| 2017/0007765 | A1* | 1/2017 | Cowe | A61M 5/2033 |
| 2017/0232204 | A1* | 8/2017 | Knapp | A61M 5/347 604/66 |
| 2017/0246383 | A1* | 8/2017 | Lanier, Jr. | A61M 5/14248 |
| 2017/0286638 | A1* | 10/2017 | Searle | G16H 40/63 |
| 2018/0008778 | A1* | 1/2018 | Erbstein | A61M 5/3155 |
| 2018/0028760 | A1* | 2/2018 | Gugl | A61M 5/3157 |
| 2018/0200452 | A1* | 7/2018 | Marcoz | G01D 5/145 |
| 2019/0091412 | A1* | 3/2019 | Gabriel | A61M 5/31546 |
| 2019/0217022 | A1* | 7/2019 | Gentz | A61M 5/20 |
| 2019/0240398 | A1* | 8/2019 | Seitz | A61M 5/1413 |
| 2019/0344019 | A1* | 11/2019 | Subramony | A61M 5/31568 |
| 2020/0139053 | A1* | 5/2020 | Faught | A61M 5/24 |
| 2020/0276390 | A1* | 9/2020 | Song | A61M 5/2033 |
| 2021/0077723 | A1* | 3/2021 | Marcoz | A61M 5/31575 |

FOREIGN PATENT DOCUMENTS

| | | | | |
|---|---|---|---|---|
| CN | 106039478 | | 10/2016 | |
| EP | 0277464 | | 8/1988 | |
| EP | 2552511 | B1* | 4/2014 | A61M 5/002 |
| EP | 3021243 | A1* | 5/2016 | G06F 19/3462 |
| EP | 3058973 | A1* | 8/2016 | A61M 5/31 |
| EP | 3085404 | | 10/2016 | |
| EP | 3085404 | A1* | 10/2016 | A61M 5/20 |
| EP | 3088026 | A1* | 11/2016 | A61M 5/20 |
| EP | 3184137 | | 6/2017 | |
| JP | 2014-520617 | | 8/2014 | |
| JP | 2014-531283 | | 11/2014 | |
| JP | 2017-534386 | | 11/2017 | |
| WO | WO 2005/115513 | | 12/2005 | |
| WO | WO-2011117212 | A1* | 9/2011 | A61B 5/14532 |
| WO | WO-2012046199 | A1* | 4/2012 | A61M 5/20 |
| WO | WO 2012/158135 | | 11/2012 | |
| WO | WO 2013/010893 | | 1/2013 | |
| WO | WO 2013/050535 | | 4/2013 | |
| WO | WO 2013/085453 | | 6/2013 | |
| WO | WO-2014111337 | A1* | 7/2014 | A61M 5/24 |
| WO | WO-2014173773 | A1* | 10/2014 | A61M 5/24 |
| WO | WO-2015001008 | A1* | 1/2015 | A61M 5/24 |
| WO | WO-2016005483 | A1* | 1/2016 | G06K 9/222 |
| WO | WO-2016023846 | A2* | 2/2016 | A61M 5/24 |
| WO | WO 2016/064916 | | 4/2016 | |
| WO | WO-2016131974 | A1* | 8/2016 | A61M 5/20 |
| WO | WO 2017/050781 | | 3/2017 | |

OTHER PUBLICATIONS

PCT International Search Report and Written Opinion in International Appln. No. PCT/EP2018/086099, dated Mar. 1, 2019, 14 pages.

* cited by examiner

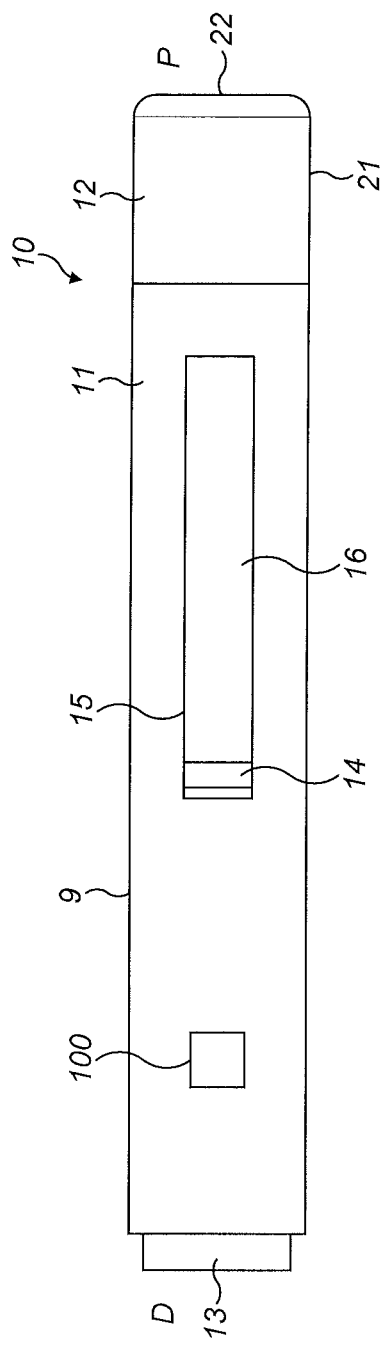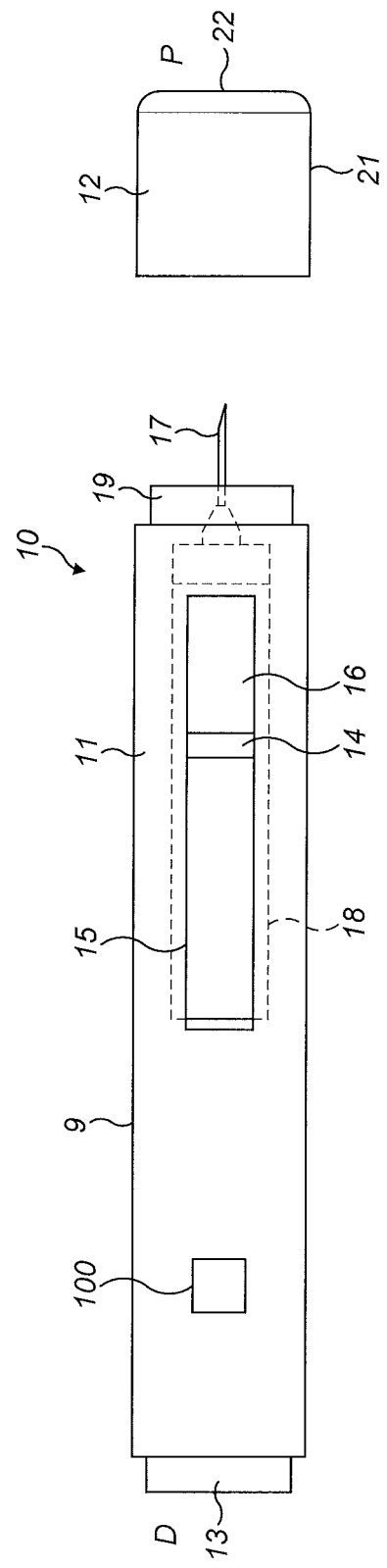

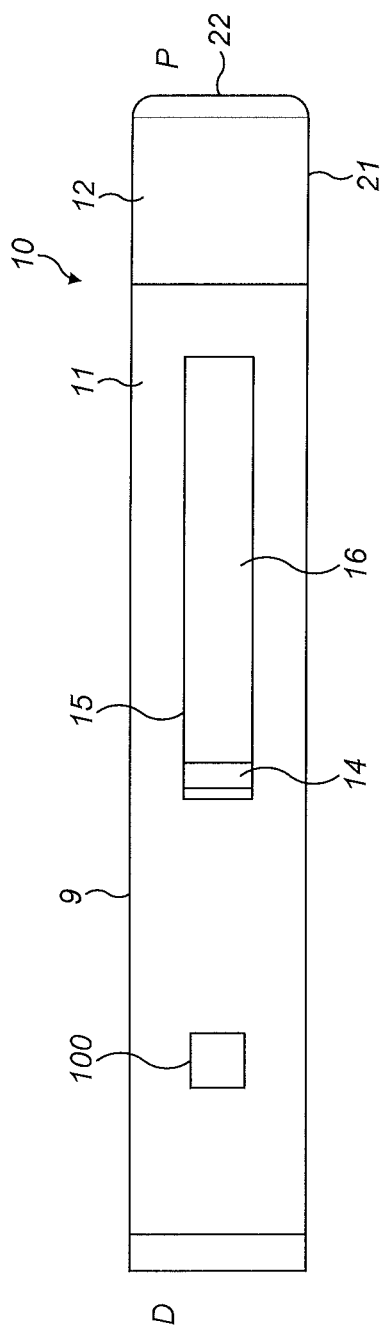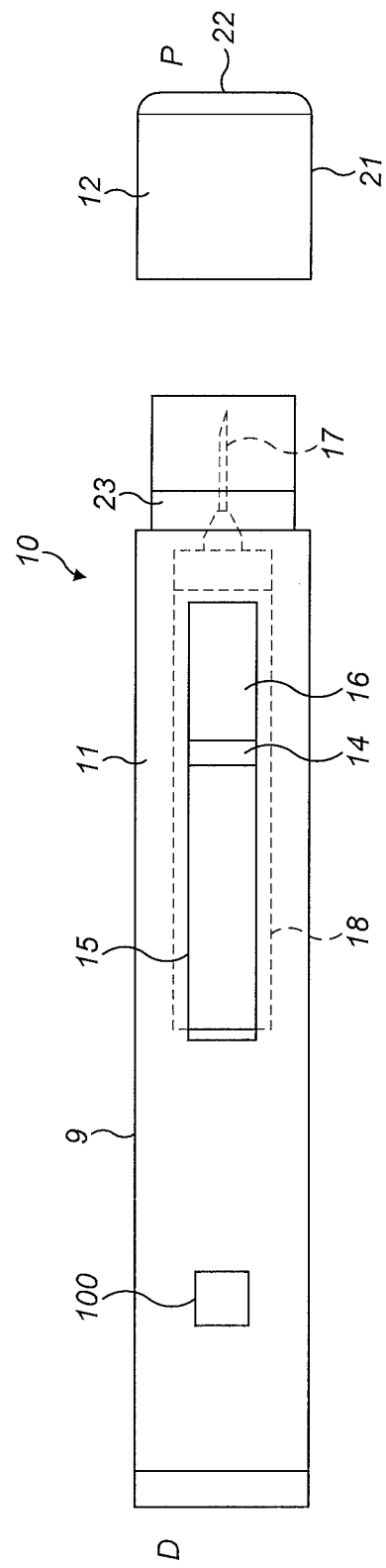
FIG. 1C
FIG. 1D

SENSOR DEVICE FOR ATTACHMENT TO AN INJECTION DEVICE

CROSS REFERENCE TO RELATED APPLICATIONS

The present application is the national stage entry of International Patent Application No. PCT/EP2018/086099, filed on Dec. 20, 2018, and claims priority to Application No. EP 17306951.9, filed on Dec. 28, 2017, the disclosures of which are incorporated herein by reference.

TECHNICAL FIELD

The present disclosure relates to a device configured to retain an injection device or syringe, to provide information to a user during an injection procedure and to remind a user when a medicament injection is due (e.g. injection monitoring).

BACKGROUND

A variety of diseases exists that require regular treatment by injection of a medicament. Such injection can be performed by using injection devices, which are applied either by medical personnel or by patients themselves.

Injection devices (i.e., devices capable of delivering medicaments from a medication container) typically fall into two categories—manual devices and auto-injectors.

Injection devices can also either be disposable, whereby the device is intended to be discarded after typically one injection operation, or re-usable, whereby the device is intended to be used for multiple injection operations.

In a manual device—the user must provide the mechanical energy to drive the fluid through the needle. This is typically done by some form of button/plunger that has to be continuously pressed by the user during the injection. There are numerous disadvantages for the user from this approach. If the user stops pressing the button/plunger, then the injection will also stop. This means that the user can deliver an under-dose if the device is not used properly (i.e., the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, allergies, hormone therapies, anticoagulants etc. Auto-injector devices can be used to deliver a single dose of a particular life-saving drug. For example they are often prescribed to people who are at risk for anaphylaxis. They are also often used in the military to protect personnel from chemical warfare agents. Alternatively, auto-injectors are used to administer medicaments according to a prescribed therapeutic schedule for people suffering from Multiple Sclerosis, Rheumatoid Arthritis, Anemia, e.g.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Forces required of the user/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

Auto-injectors may be disposable or single use devices which may only be used to deliver one dose of medicament and which have to be disposed of after use. Other types of auto-injectors may be reusable. Usually they are arranged to allow a user to load and unload a standard syringe. The reusable auto-injector may be used to perform multiple parenteral drug deliveries, whereas the syringe is disposed after having been spent and unloaded from the auto-injector. The syringe may be packaged with additional parts to provide additional functionality.

In a typical scenario a disease can be treated by patients themselves by injection of medicament doses using an auto-injector, for example on a daily, weekly, bi-weekly, or monthly basis.

SUMMARY

According to a first aspect of the disclosure, there is provided a supplementary device configured to be releasably attached to a drug delivery device, the supplementary device comprising: a first non-contact sensor configured to output signals indicative of the position of a first moveable component within the drug delivery device; and a processor configured to: receive the signals output from the first non-contact sensor; determine based on the signals the moment at which the drug delivery device changes from a pre-ejection state to a post-ejection state; in response to determining that the drug delivery device has changed from the pre-ejection state to the post ejection state, cause a display of the supplementary device to visually indicate that a user should hold the drug delivery device in its current position for a predetermined period of time.

In some embodiments, the first non-contact sensor is a Hall effect sensor and the supplementary device further comprises a permanent magnet. In some embodiments, the Hall effect sensor is configured to output signals indicative of the position of the permanent magnet.

In some embodiments, the first non-contact sensor is a Hall effect sensor or an anisotropic magnetoresistive sensor. The first moveable component may comprise a ferromagnetic material, such as a ferrous material or a permanent magnet and the Hall effect sensor or anisotropic magnetoresistive sensor is configured to output signals indicative of the position of the ferromagnetic material. In some embodiments, the first moveable component comprises a permanent magnet and the Hall effect sensor or anisotropic magnetoresistive sensor is configured to output signals indicative of the position of the permanent magnet.

In some embodiments, the processor is configured to determine, based on the signals from the first non-contact sensor, whether the drug delivery device is in a pre-ejection state or a post-ejection state.

In some embodiments the signals from the first non-contact sensor are generated by changes in a magnetic field passing through the Hall effect sensor.

In some embodiments, the first non-contact sensor is an inductive sensor or a piezoelectric sensor.

In some embodiments, the first non-contact sensor is configured to detect movement of a needle shield from a needle of the drug delivery device.

In some embodiments, the supplementary device further comprises a second non-sensor configured to output signals indicative of the position of a second moveable component within the drug delivery device.

In some embodiments, the second non-contact sensor is a Hall effect sensor. In some embodiments, the Hall effect sensor is configured to output signals indicative of the position of the permanent magnet of the second component.

In some embodiments, the second non-contact sensor is an anisotropic magnetoresistive sensor.

In some embodiments, the processor is configured to respond to determining that a time of scheduled injection is due by changing the appearance of the supplementary device in order to become more noticeable.

In some embodiments, the processor is configured to respond to receive a user input by activating the display.

In some embodiments, when the drug delivery device is in the pre-ejection state, the user input causes the display to visually indicate that the user should remove a needle cap, insert a needle of the drug delivery device into the user and begin medicament injection.

In some embodiments, the drug delivery device is configured to respond to detection of activation of an ejection process by causing the display to visually indicate an injection is in progress.

In some embodiments, the processor is configured to determine, based on the signals from the second non-contact sensor, whether the drug delivery device is in a pre-activation state or a post-activation state.

In some embodiments, the supplementary device further comprises a locking sensor configured to output signals indicative of whether the supplementary device is secured to the drug delivery device or not.

In some embodiments, the supplementary device further comprises a wireless unit configured to transmit data to one or more external devices.

In some embodiments, the supplementary device further comprises a light emitting user input configured to change appearance.

In some embodiments, the supplementary device is configured to determine a time at which the user's next medicament dose is due.

In some embodiments, the supplementary device further comprises a light emitting user input configured to change appearance at the time at which the user's next medicament dose is due.

In some embodiments, the supplementary device further comprises an audio module and wherein the visual indication that a user should hold the drug delivery device in its current position for a predetermined period of time is accompanied by an audible indication from the audio module.

In some embodiments, the indication that the user should hold the drug delivery device in its current position for a predetermined period of time comprises a countdown timer.

In some embodiments, the supplementary device further comprises at least one memory and wherein the processor is configured to cause information relating to a last performed ejection process to be stored in the memory upon determining that the drug delivery device has changed from a pre-ejection state to a post-ejection state, wherein the information comprises at least a time stamp associated with the last performed ejection process.

In some embodiments, the processor is further configured to produce a reminder signal when the time of the user's next medicament dose occurs.

In some embodiments, the processor has access to or is configured to calculate a medical regimen associated with a user of the supplementary device, the medical regimen comprising at least a series of times at which an a medicament dose is due and wherein the processor is configured to cause a reminder signal to be produced when a next medicament dose is due according to the medical regimen.

In some embodiments, the supplementary device is further configured to send the reminder signal to one or more external devices.

In some embodiments, the supplementary device further comprises an optical sensor configured to read information visible on a housing of the injection device, the information identifying a medicament contained in the drug delivery device.

In some embodiments, the drug delivery device is a powered auto-injector.

According to a second aspect of the disclosure, there is provided a method of operating a supplementary device configured to be releasably attached to a drug delivery device, the method comprising: using a first non-contact sensor to output signals indicative of the position of a first moveable component within the drug delivery device; receiving the signals output from the first non-contact sensor at a processor; the processor determining based on the signals the moment at which the drug delivery device changes from a pre-ejection state to a post-ejection state; and in response to determining that the drug delivery device has changed from the pre-ejection state to the post ejection state, causing a display of the supplementary device to visually indicate that a user should hold the drug delivery device in its current position for a predetermined period of time.

According to a third aspect, a system is provided comprising the supplementary device of the first aspect is provided and the drug delivery device.

In some embodiments, according to the third aspect, the first moveable component is a resilient member arranged to change between a first configuration and a second configuration.

In some embodiments, according to the third aspect, the drug delivery device comprises a flexible arm configured to retain the first moveable component in the first configuration when it is in a first position and wherein the flexible arm is retained in the first position by contact with a part of a plunger of the drug delivery device in the pre-ejection state. In some embodiments, the first moveable component is a part of a plunger of the drug delivery device.

In some embodiments, the drug delivery device comprises a cartridge or syringe containing a medicament.

According to a further aspect, there is provided a method of operating the system according to the third aspect, the method comprising: removing a needle shield from the drug delivery device, inserting a needle of the drug delivery device into the user, operating a trigger of the medicament delivery device so as to move a piston and dispense a medicament.

The correct administration of drugs and its termination is important for the safety and efficacy of the drug (pharmacovigilance). Failures in administration through the user can be minimized by monitoring of the injection device and the application time. The re-usable add-on device is suitable for use with one shot auto-injectors and may record the injection history, monitor the dose administration and aid the patient in performing the injection correctly and on time. The device may reduce patient error related to the user forgetting the correct day of maturity for their next injection or forgetting to carry out holding time (dwell time) after injection. The device may also reduce in needle clogging and/or device stalling.

BRIEF DESCRIPTION OF THE FIGURES

FIG. 1A shows a side view of an injection device;

FIG. 1B shows a side view of the injection device of FIG. 1A with a cap detached;

FIG. 1C shows a side view of a different injection device to the injection device shown in FIGS. 1A and 1B, whilst FIG. 1D shows a side view of the injection device of FIG. 1C with a cap detached;

DETAILED DESCRIPTION OF THE FIGURES

Figure 2A:
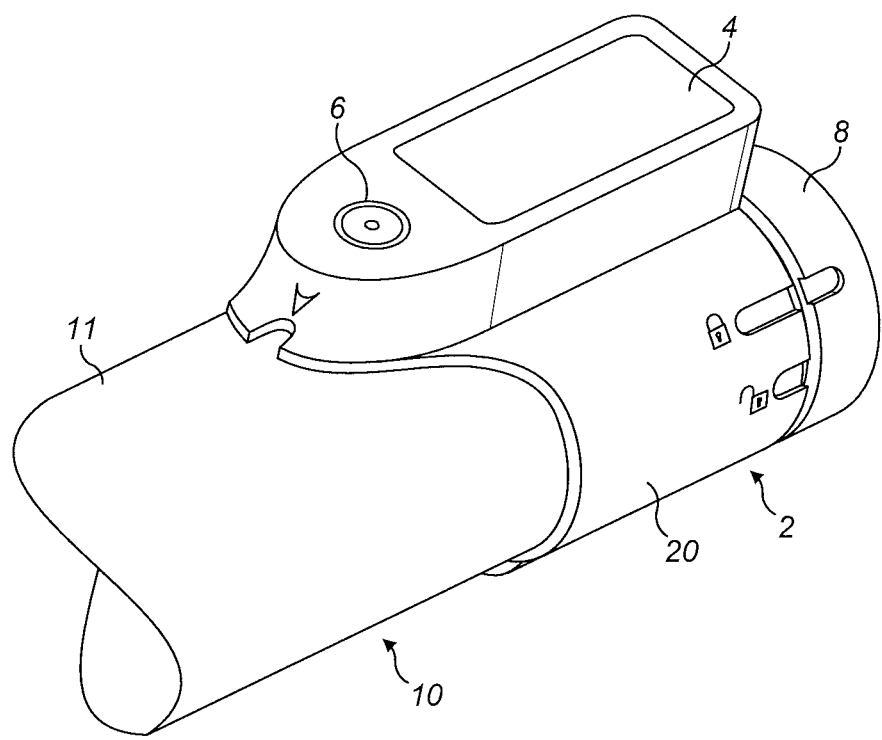
FIGS. 2a and 2b show a perspective view of a supplementary device releasably attached to the injection device of FIGS. 1a and 1b.

In the following, embodiments of the present disclosure will be described with reference to auto-injectors. The present invention is however not limited to such application and may equally well be deployed with injection devices that eject other medicaments, or with other types of drug delivery devices, such as syringes, pre-filled syringes, needleless injectors and inhalers.

An injection device 10 (also referred to herein as a drug delivery device 10) according to embodiments will now be described with reference to FIGS. 1A and 1B. In some embodiments, the injection device 10 is a single use auto-injector 10. The auto-injector 10 has a proximal end P and a distal end D. The proximal end P is directed towards the injection site of a patient during an injection while the distal end D is directed away from the injection site.

The auto-injector 10 comprises a body 9 and a cap 12 (also referred to herein as the outer needle cap or ONC 12). The body 9 comprises an outer housing 11. The outer housing 11 is an elongate tube. The outer housing 11 may also include a cartridge holder or syringe holder (not shown) which supports a cartridge or syringe 18 containing liquid medicament 16.

The outer housing 11 also houses a dispense mechanism (not shown) for causing dispensing of the medicament 16 during injection. The dispense mechanism may comprise a drive mechanism.

A hollow needle 17 communicates with an interior volume of the syringe 18 and serves as a conduit for liquid medicament 16 during injection. The needle 17 and the syringe 18 are in a fixed position relative to each other and to the body 9. A stopper, plunger, piston or bung 14 is moveable within the syringe 18 to expel medicament contained within the syringe 18 through the needle 17 under action of the dispense mechanism.

The dispense mechanism is mechanically coupled to the piston 14 of syringe 18. The dispense mechanism is configured to move the piston axially along the syringe 18 in a proximal direction to dispense medicament 16 through the needle 17. The dispense mechanism includes components that cooperate to apply a force to the piston 14 in response to an actuation input provided by a user. For example, the piston 14 may be spring-loaded. Here, the actuation input that triggers application of a force to the piston 14 is received by way of a dose dispense button 13 that is located at the distal end of the auto-injector 10. The dispense mechanism is mechanically coupled to the dispense button 13.

The body 9 also comprises a cap support 19 at the proximal end of the outer housing 11. The cap support is concentric with the outer housing 11 and may have a smaller diameter. The cap support 19 extends from the proximal end of the housing 11. The ONC 12 is received over the cap support 19 to close the proximal end of the body 9 and to cover the needle 17. The ONC 12 comprises a cylindrical wall 21 and an end wall 22. With the ONC 12 located on the body 9, as shown in FIG. 1A, an internal surface of the cylindrical wall 21 abuts an external surface of the cap support 19 in tightly abutting relation so that the ONC 12 is retained thereon in an attached position.

To inject the medicament 16, the ONC 12 is removed from the device 10 by the user, resulting in the arrangement shown in FIG. 1B. Next, the proximal end of the auto-injector 10 is placed against an injection site of a patient, which may be the user or another person. The user then actuates the dispense button 13. This causes the dispense mechanism to force the piston 14 to expel medicament from the syringe 18 through the needle 17 into the injection site of the patient.

FIGS. 1C and 1D show another type of auto-injector which can be used in some other embodiments of the disclosure. The auto-injector 10 has many of the same components as in the auto-injector of FIGS. 1A and 1B, and these will not be described again. The dispense mechanism of this auto-injector is different. Here, the actuation input that triggers application of a force to the piston 14 is received by way of a sleeve 23 which is configured to trigger operation of the auto-injector. The dispense mechanism is mechanically coupled to the sleeve 23. The sleeve is concentric with the outer housing 11 and has a smaller diameter. The sleeve 23 extends from the proximal end of the housing 11 and beyond the point of the needle 17 before the auto-injector is activated. The ONC 12 is received over the sleeve 23 to close the proximal end of the body 9. The auto-injector has no dispense button.

To inject the medicament 16, the ONC 12 is removed from the device 10 by the user, resulting in the arrangement shown in FIG. 1D. Next, the proximal end of the sleeve 23 is placed against an injection site of a patient, which may be the user or another person. The user then presses the auto-injector down with force. This causes the sleeve 23 to move distally into the auto-injector and to trigger the dispense mechanism. The dispense mechanism forces the piston 14 to expel medicament from the syringe 18 through the needle 17 into the injection site of the patient.

After a user injects a quantity of medicament into their skin, it is advantageous for the needle to be left in position for a short time (e.g. 5-20 seconds). This allows the medicament to be diffused away from the injection site by action of the user's blood flow. This is often referred to as "dwell time". If the needle is removed too soon after an injection, it can result in medicament being expressed from the injection site and the user therefore not receiving a full dose.

The syringe 18 is transparent and a window 15 is provided in the housing 11 coincident with the syringe 18 so that the medicament 16 contained within the syringe 18 is visible. A user of the auto-injector is able, by inspection, to determine whether the entire quantity of medicament 16 has been ejected from the syringe 18 during the injection.

A label is provided on the housing 11. The label includes information 100 about the medicament included within the injection device 10, including information identifying the medicament. The information 100 identifying the medicament may be in the form of text. The information 100 identifying the medicament may also be in the form of a color. The information 100 identifying the medicament may also be encoded into a barcode, QR code or the like. The information 100 identifying the medicament may also be in the form of a black and white pattern, a color pattern or shading.

FIG. 2a is a schematic illustration of an embodiment of a supplementary device 2 releasably attached to injection device 10 of FIG. 1. The supplementary device 2 is suitable for use with both the auto-injector shown in FIGS. 1A and 1B and in FIGS. 1C and 1D. Supplementary device 2 comprises a housing 20 configured to embrace the housing 11 of injection device 10 of FIG. 1, so that the injection device 10 is at least partially retained within the supplementary device 2, but is nevertheless removable from the supplementary device 2, for instance when injection device 10 is empty and has to be replaced. The injection device 10 and supplementary device 2 may optionally comprise co-operating alignment features to ensure that the supplementary device 2 is correctly orientated and positioned with respect to the injection device 10.

Figure 2B:
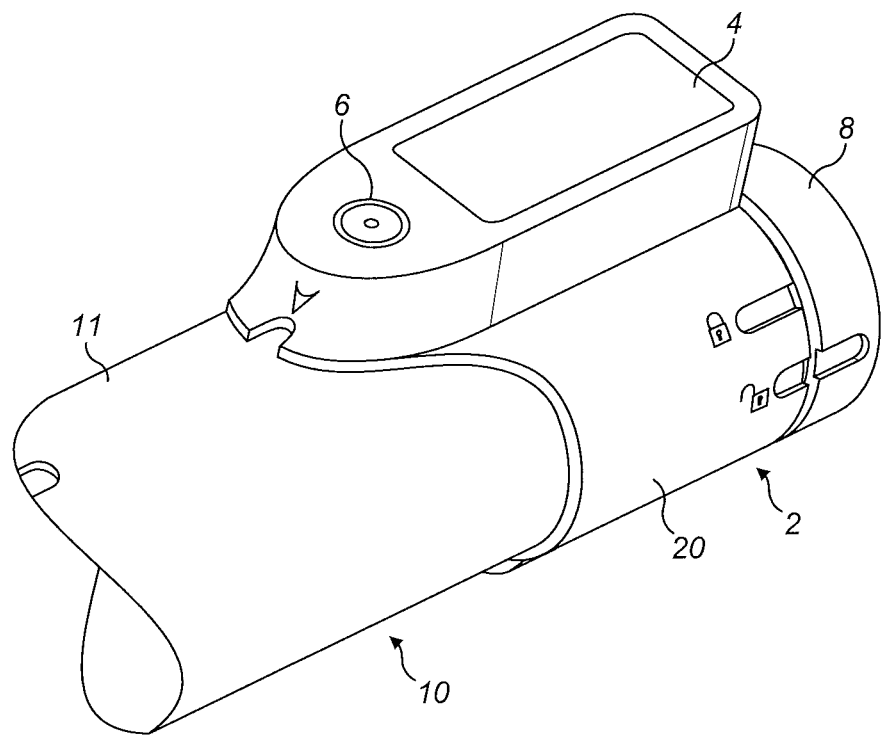

The supplementary device 2 has an attachment mechanism 8 for securing and un-securing the supplementary device 2 with the injection device 10. The attachment mechanism 8 may be rotatable relative to the main body 20 of the supplementary device 2 between a locked and an unlocked position. FIG. 2a shows the attachment mechanism 8 in a locked position. FIG. 2b shows the attachment mechanism 8 in an unlocked position.

Information is displayed via display unit 4 of supplementary device 2. The display unit 4 may be a color LCD screen. The display unit may be a touch sensitive screen. For example, the display unit 4 may indicate the time and date of the next scheduled injection for the user of the supplementary device 2. During operation of the injection device 10, the supplementary device 2 may also display information to assist the user, as will be described in greater detail below.

The supplementary device 2 may also comprise at least one user input 6 such as a touch sensitive button. The user input 6 may comprise one or more LEDs. These may form a ring around the button and/or illuminate the whole of the button. The user input 6 may allow a user to turn on/off supplementary device 2, to trigger actions (for instance to cause establishment of a connection to or a pairing with another device, and/or to trigger transmission of information from supplementary device 2 to another device), or to confirm something.

Figure 3:
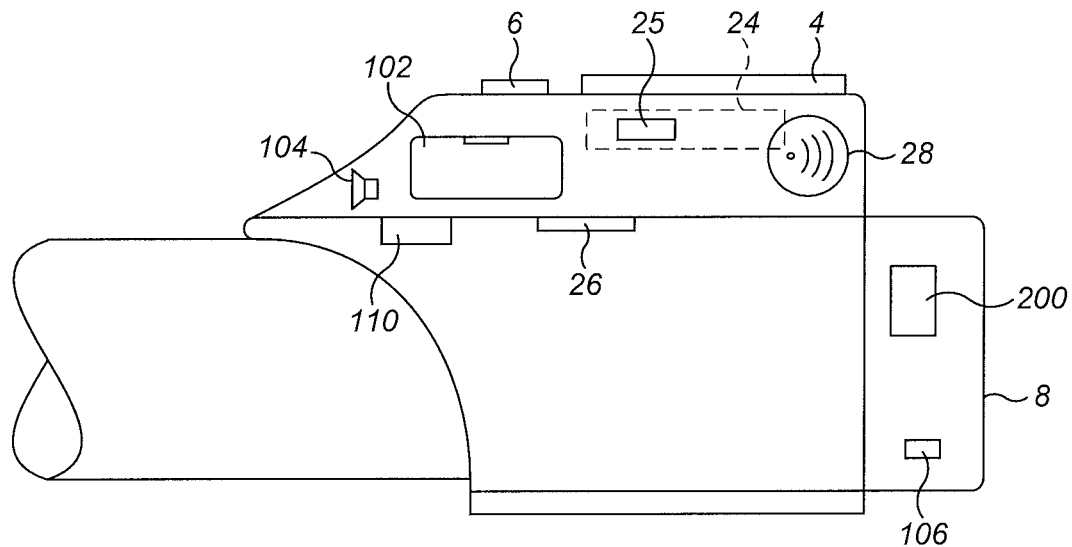
FIG. 3 shows a side view of the supplementary device of FIGS. 2a and 2b and an attached injection device and illustrates some of the major internal and external components of the supplementary device.

FIG. 3 illustrates some of the major internal and external components of the supplementary device 2 in a state where it is attached to injection device 10 shown in FIGS. 1A and 1B. Externally, the supplementary device 2 comprises the display unit 4, the user input 6, attachment mechanism 8 and a battery compartment 102.

Internally, the supplementary device 2 comprises electronics 24. The electronics 24 comprise at least a processor 25 and memory. The electronics 24 may comprise both a program memory and a main memory. The processor 25 may for instance be a microprocessor, a Digital Signal Processor (DSP), Application Specific Integrated Circuit (ASIC), Field Programmable Gate Array (FPGA) or the like. The processor 25 executes program code (e.g. software or firmware) stored in the program memory, and uses a main memory, for instance to store intermediate results. The main memory may also be used to store a logbook on performed ejections/injections. The program memory may for instance be a Read-Only Memory (ROM), and the main memory may for instance be a Random Access Memory (RAM).

The supplementary device 2 also comprises a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fiber connection. When data is transmitted, the units of the data (values) transferred may be explicitly or implicitly defined. For instance, in case of an insulin dose, always International Units (IU) may be used, or otherwise, the used unit may be transferred explicitly, for instance in coded form. The transmitted data also includes a time stamp associated with an injection.

The supplementary device 2 also comprises an audio module 104 configured to provide audio feedback to a user of the supplementary device 2. Both the wireless unit 28 and audio module 104 may be coupled to and controlled by the electronics 24. The supplementary device 2 may optionally comprise a locking sensor 106 configured to sense whether the attachment mechanism is in the locked position or the unlocked position.

The supplementary device 2 may also comprise an optical sensor 26 for reading the information 100 identifying the medicament. The information 100 identifying the medicament may be the color of the housing 11 of the injection device, or the color of an area of the housing or a label affixed to the housing. In these embodiments, the optical sensor 26 may be a simple photometer configured to detect the color. In some other embodiments, the information 100 identifying the medicament may be a QR code, or other similar encoded information and the optical sensor 26 may be a camera or QR code reader. Further, one or more light sources may be provided to improve reading of optical sensor 26. The light source may provide light of a certain wavelength or spectrum to improve color detection by optical sensor 26. The light source may be arranged in such a way that unwanted reflections, for example due to the curvature of the housing 11, are avoided or reduced. In an example embodiment, the optical sensor 26 is a camera unit configured to detect a code 100 (for instance a bar code, which may for instance be a one- or two-dimensional bar code) related to the injection device and/or the medicament contained therein. This code 100 may for instance be located on the housing 11 or on a medicament container contained in injection device 10, to name but a few examples. This code 100 may for instance indicate a type of the injection device and/or the medicament, and/or further properties (for instance an expiration date). This code 100 may be a QR code 100. The QR code is in general black and white and thus no color detection is required on the part of the optical sensor 26. This allows the optical sensor 26 to be simple and cheap to manufacture.

The processor 25 may be configured to check the information 100 read by the optical sensor 26 against pre-stored information in order to verify that the user is injecting the correct medicament. If the processor 25 does not recognize the information 100 or recognizes the information 100 as indicating a different medicament to that which the user should be receiving at that time, then the supplementary device 2 may produce an alarm signal. The alarm signal may comprise words or graphics displayed on the display unit 21 or sound produced by the audio module 104. Alternatively, or in addition, the supplementary device 2 may send an alarm signal to an external device via wireless unit 28.

The supplementary device 2 comprises an injection device status sensor 110 (also referred to herein as a non-contact sensor or first non-contact sensor). The status sensor 110 may take a number of forms, described in greater detail with respect to FIGS. 4a to 7b below. The status sensor 110 is configured to output signals indicative of the positions of one or more components within the injection device 10. The status sensor 110 may be referred to as a non-contact sensor, since it is able to sense the absolute position and/or movement of components within the attached injection device 10 without contact between the sensor 110 and any of the components sensed. The electronics 24 receive these signals and infer an operational state of the injection device 10 and cause information regarding the timing of the operation of the injection device 10 to be recorded in the main memory and/or transmitted to an external device via the wireless unit 28. The exact position of the first non-contact sensor 110 within the supplementary device 2 depends upon the position and movement range of the moveable component of the injection device being measured. In the embodiments described with reference to FIGS. 4a to 7b below, the moveable component is close to the cylindrical part of the housing 11 of the injection device 10 and separated from the distal end, e.g. approximately one quarter of the length of the injection device from the distal end. Therefore, the first non-contact sensor 110 is positioned adjacent the cylindrical part of the housing 11, towards the proximal end of the supplementary device 2. In some embodiments, the first non-contact sensor is configured to detect movement of the needle cover.

The supplementary device 2 may optionally comprise a second non-contact status sensor 200. The second non-contact status sensor 200 may take a number of forms, as described in greater detail with respect to FIGS. 8a-8c below. The second non-contact status sensor 200 may be arranged within the supplementary device 2 so as to be adjacent the proximal end face of the attached injection device 10. The second non-contact status sensor 200 may be configured to output signals which represent the absolute position of a second moveable component within the injection device 10 which is also located near to the proximal end face of the injection device 10.

Figure 4A:
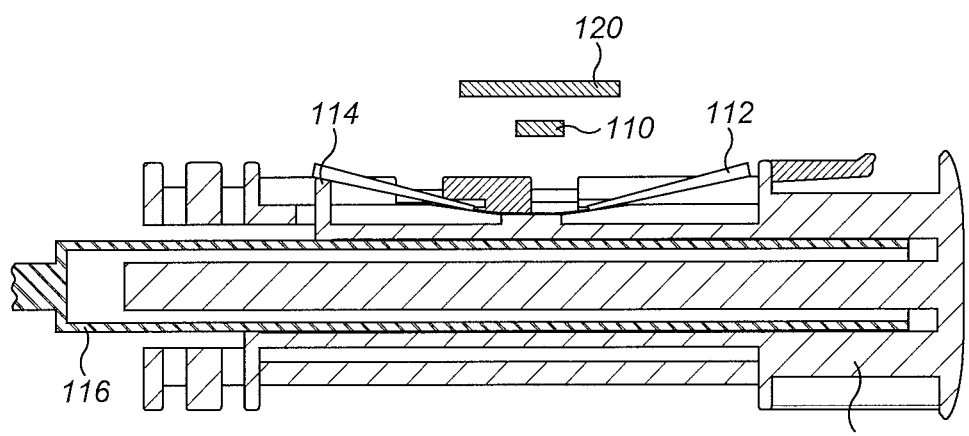
FIGS. 4a and 4b show a cut-away view of an injection device and illustrate a first example of a non-contact status sensor of a supplementary device.
Figure 4B:
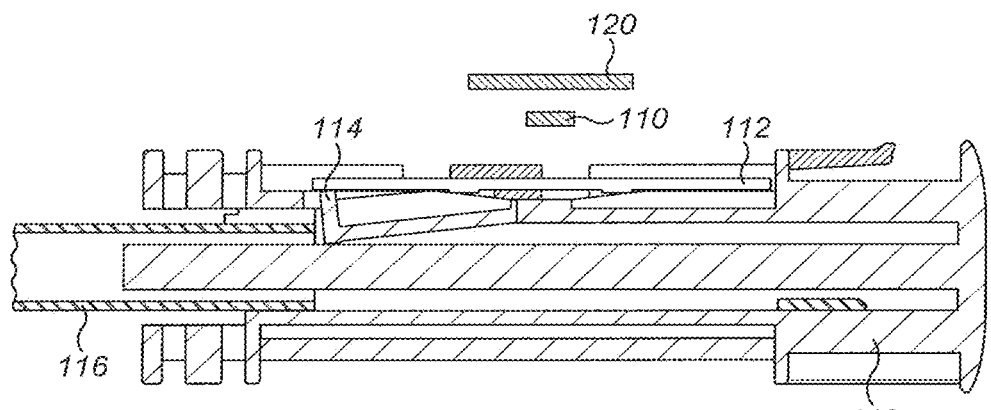

FIGS. 4a and 4b show an example of how the status sensor 110 detects a change in the status of the injection device according to some embodiments of the disclosure.

FIG. 4a shows diagrammatically a cut-away through the injection device 10 of FIGS. 1A and 1B when the injection device is in a pre-ejection configuration and a post ejection configuration (also referred to as pre-activation and post-activation). FIGS. 4a and 4b omit the outer housing 11 and some other components of the injection device 10 for clarity. The injection device 10 comprises a drive spring (not shown), which is pre-compressed during assembly of the injection device 10. The drive spring is maintained in this pre-compressed state until an injection is started. When a user triggers an injection operation by activating the needle sleeve 19 or by pressing dose dispense button 13, the dispense mechanism is released and the drive spring to decompresses so as to dispense medicament from the syringe 18.

The injection device 10 comprises a resilient member 112 (also referred to herein as a moveable component 112). The resilient member 112 is designed to change between a first configuration and a second configuration and is biased towards the second configuration (i.e., the resilient member 112 will be in the second configuration if no external forces act on it). In the embodiments illustrated by FIGS. 4a and 4b, the resilient member 112 is a resilient sheet metal member in an elongate shape. The resilient member 112 has a groove running along the center of its long axis which allows the resilient member 112 to bend along the long axis.

Figure 5A:
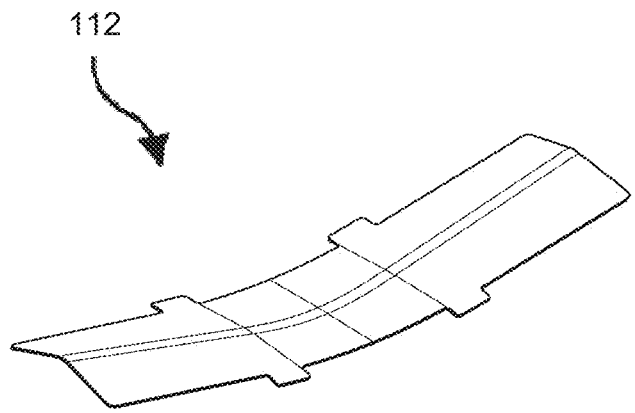
FIGS. 5a and 5b illustrate an exemplary resilient member forming part of the injection device of FIGS. 4a and 4b.
Figure 5B:
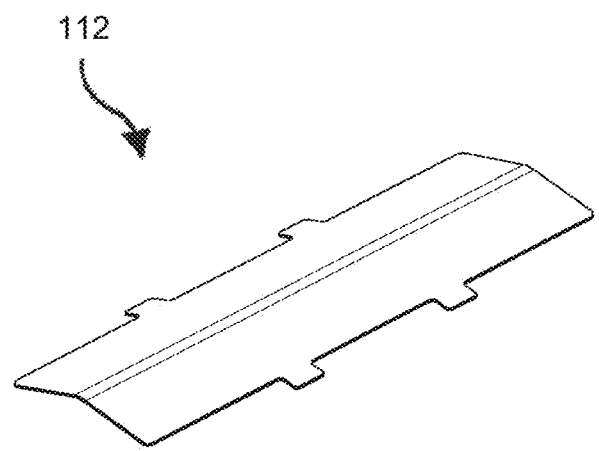

FIGS. 5a and 5b show an example of the resilient member 112. In FIG. 5a, the resilient member 112 is in the first configuration, while in FIG. 5b, the resilient member 112 is in the second configuration. The resilient member 112 may have one or more tabs on its outer edge to hold it in place within the injection device 10. The first configuration has a bent or "U" shape, such that the two ends of the resilient member 112 are bent up while the center is bent downwards. In the second configuration, the resilient member 112 is substantially flat. In both configurations, the resilient member 112 may be bent lengthways along the central groove.

Referring again to FIG. 4a, the resilient member 112 is retained in the first configuration by a flexible arm 114. The flexible arm 114 abuts the outer surface of the plunger 116 of the injection device 10 when the injection device 10 is in a pre-ejection state and during an ejection process. The flexible arm 114 may be part of an inner housing 118 of the injection device 10, or may be attached to the inner housing 118. Referring to FIG. 4b, the plunger 116 advances during an ejection process to expel the medicament contained in the syringe 18. At the end of the ejection process, the plunger 116 advances beyond the flexible arm 114. The flexible arm 114 is biased towards the plunger 116 and so moves towards the center of the injection device 10 once it no longer abuts against the plunger 116. This releases the force on the resilient member 112, which changes to the second configuration.

The status sensor 110 of the supplementary device 2 is shown schematically. All other components of the supplementary device 2 are omitted for clarity. In the embodiments of FIGS. 4a and 4b, the status sensor 110 is a Hall sensor 110. The supplementary device 2 also comprises a permanent magnet part 120 located near the Hall sensor 110. With the arrangement shown, the voltage output of the Hall sensor 110 is dependent on the configuration of the resilient member 112. When the resilient member 112 is in the second configuration (FIG. 4b), the resilient member 112 is closer to the permanent magnet 120. As the resilient member 112 is at least partially made of a ferrous metal (i.e., a ferromagnetic material) or a material that comprises ferrite (i.e., a ferromagnetic material), this changes the magnetic flux density at the Hall sensor 110. There is therefore a change in the output voltage of the Hall sensor 110 at the moment when the resilient member 112 changes from the first to the second configuration. The electronics 24 receive the signals output from the sensor 110 and determine the time at which the change took place, i.e., the time at which the ejection process was completed. This information is recorded in the memory of the supplementary device 2 and may also be transmitted to an external device by the wireless unit 28.

Figure 6A:
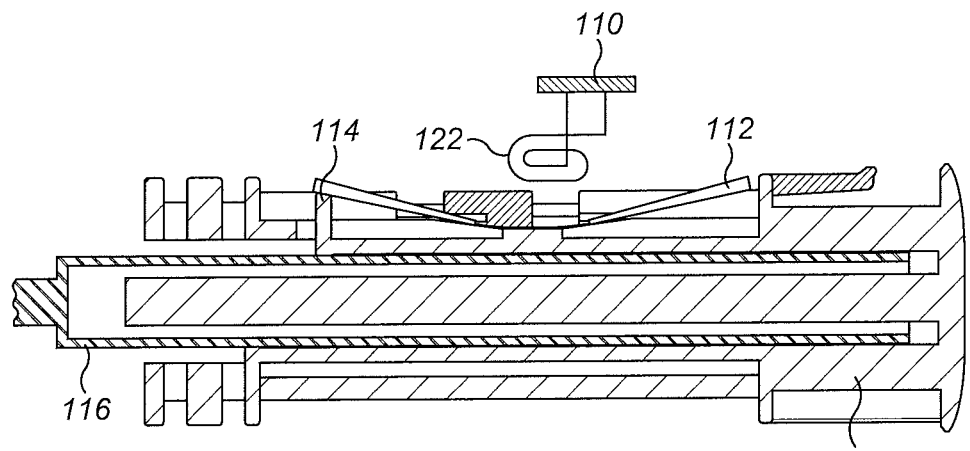
FIGS. 6a and 6b show a cut-away view of an injection device and illustrate a second example of a non-contact status sensor of a supplementary device.
Figure 6B:
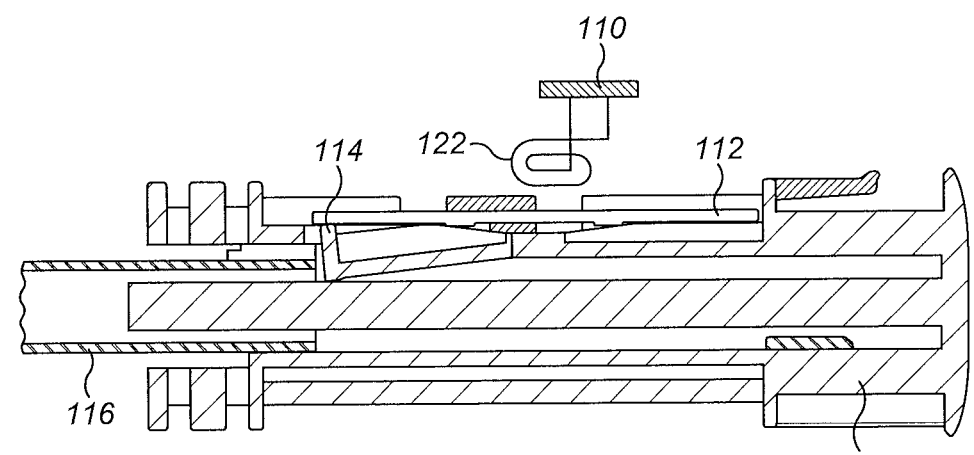

Referring to FIGS. 6a and 6b, an alternative example of the status sensor 110 according to some other embodiments of the disclosure is shown. The structure and operation of the injection device 10 of FIGS. 1A and 1B and the resilient member 112 are the same as described above and will not be described in detail again here. In this example, the sensor is an inductive sensor 110 (also referred to as an Eddy current sensor 110). The Eddy current sensor 110 comprises a detection circuit and a coil 122 coupled to the detection circuit. When the resilient member 112 changes from the first configuration to the second configuration, it induces a current in the coil 122 which is detected by the circuit. The resilient member 112 may be made of a ferrite material, such as a ferritic stainless steel, such that its movement induces a current in the coil 122. Again, the electronics 24 receive the signals output from the sensor 110 and determine the time at which the resilient member 112 changed configuration.

Figure 7A:
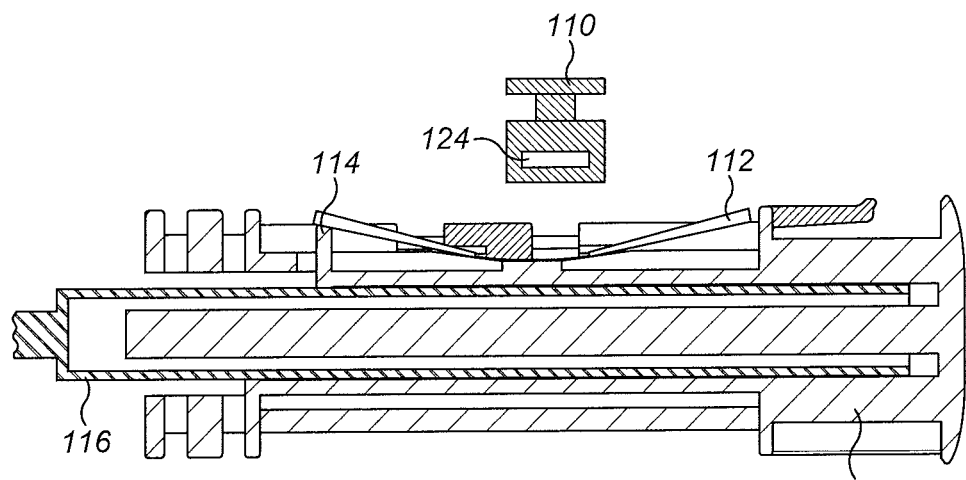
FIGS. 7a and 7b show a cut-away view of an injection device and illustrate a third example of a non-contact status sensor of a supplementary device.
Figure 7B:
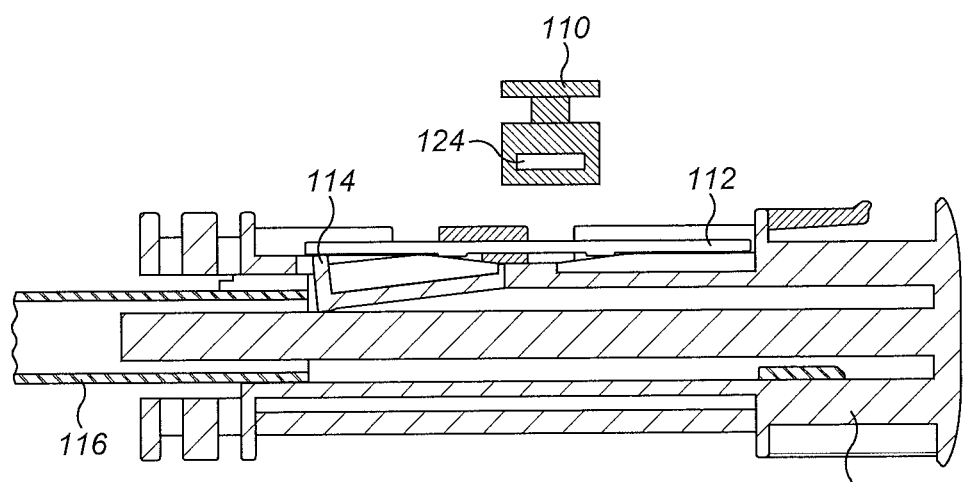

FIGS. 7a and 7b show a third example of the status sensor 110 according to some further embodiments of the disclosure. The structure and operation of the injection device 10 of FIGS. 1A and 1B and the resilient member 112 are the same as described above and will not be described in detail again here. In this example, the sensor is a Piezoelectric sensor 110. The piezoelectric sensor 110 comprises a detection circuit and a piezoelectric part 124, placed close to or against the housing of the supplementary device 2. In these embodiments, the resilient member 112 is designed to make a sound, such as a sharp click, when it changes configuration. This sound produces vibrations in the piezoelectric part 124, which produces a current as a result. This current is detected by the detection circuit. Again, the electronics 24 receive the signals output from the sensor 110 and determine the time at which the resilient member 112 changed configuration.

Figure 8A:
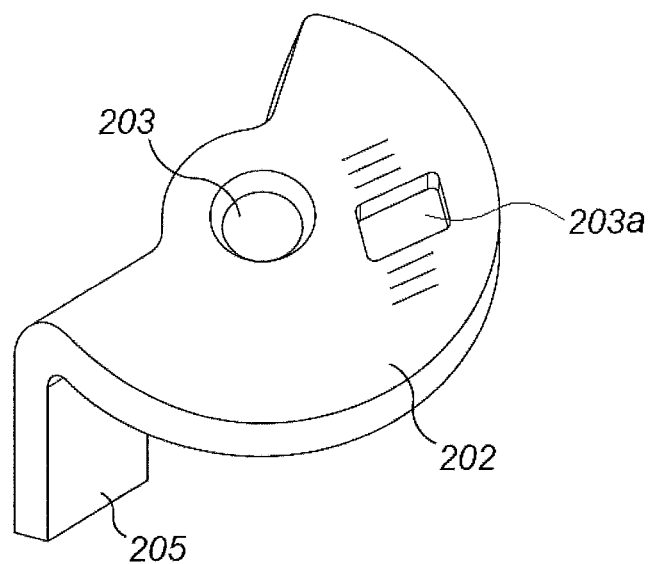
FIG. 8a shows an exemplary moveable component which may be mounted in the injection device of FIGS. 1a and 1b.
Figure 8B:
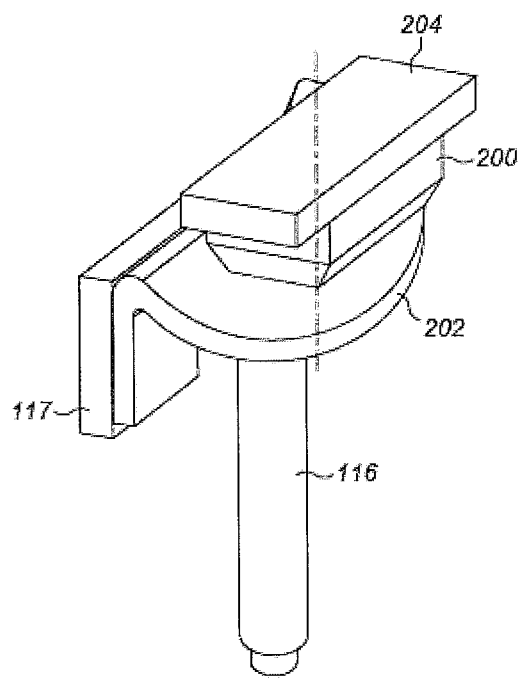
FIG. 8b shows the position of the moveable component of FIG. 8a relative to other components of the injection device and supplementary device.
Figure 8C:
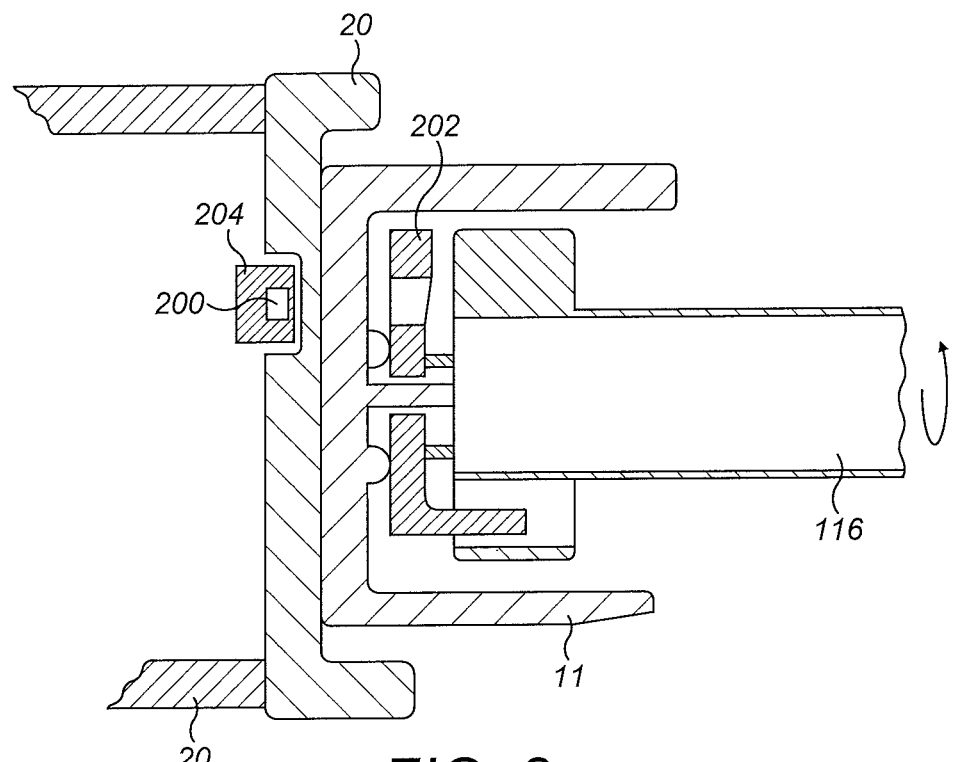
FIG. 8c is a cut-away view of the injection device and attached supplementary device showing the moveable component of FIG. 8a and a second non-contact sensor.

FIGS. 8a, 8b and 8c illustrate components of an injection device 10 which allow the second non-contact status sensor 200 to determine the status of the injection device 10. FIG. 8a shows an exemplary second moveable component 202. The second moveable component 202 has a partial disc shape with a central bore 203 for rotatably mounting the component 202 within the injection device 10. The second moveable component 202 also has a protrusion 205, extending perpendicularly from the plane of the partial disc part. The protrusion is configured to abut or otherwise engage with the plunger 116 of the injection device 10. The partial disc part of moveable component 202 further comprises an aperture or indentation 203a. The moveable component 202 is configured to rotate about an axis of rotation which runs through the bore 203 of the component 202. As the moveable component is rotated during use, the aperture 203a moves within close proximity to (e.g. directly underneath) the sensor 200 (not shown). As the aperture 203a moves past the status sensor 200, a signal is generated. In some alternative embodiments, a permanent magnet or ferritic material may replace the aperture 203a. In such embodiments, as the permanent magnet or ferritic material moves past the status sensor 200, a signal is generated.

FIG. 8b shows components of both the injection device 10 and supplementary device 2 in situ. The housings of both the injection device 10 and supplementary device 2 have been omitted for clarity. The plunger 116 has one or more wings 117 which extend radially away from the plunger axis at the proximal end of the plunger. The housing 11 of the injection device 10 has a protrusion which acts as an axis which the second moveable component 202 is rotatably mounted on. The plunger 116 is also rotatable relative to the housing 11 of the injection device 10 and may also be mounted on this protrusion. During user activation of the ejection process, the plunger 116 is rotated. The abutment between the plunger wing 117 and a second moveable component protrusion 205 causes the second moveable component 202 to rotate. Thus, the wings 117 can be said to "guide" the rotation of the second moveable component 202 because the wings engage with the protrusion 205 of the second moveable component 202 and cause rotation of the second moveable component 202. As the second moveable component 202 rotates, activation of the sensor 200 occurs as described in the following. The supplementary device 2 comprises the second non-contact status sensor 200, which in these embodiments is a Hall Sensor 200, and a permanent magnet 204. The dashed line in FIG. 8b represents the axis of magnetic flux which the second non-contact status sensor 200 is sensitive to. As the second moveable component 202 rotates, the magnetic flux detected by the second non-contact status sensor 200 changes. Once the plunger 116 has completed its rotation, the ejection process begins. At this point, the aperture 203a of the second moveable component 202 is underneath the sensor 200 and the voltage output of the Hall sensor 200 is changed. Thus the signals output by the Hall sensor 200 allow the processor 25 to determine whether the injection device 10 is in a pre-activation state or a post-activation state. The Hall sensor may alternatively be replaced by an anisotropic magnetoresistive (AMR) sensor which is also able to detect the rotational angle of the second moveable component 202.

The processor 25 is configured to control the display 4 and the user input 6 of the supplementary device 2 to guide a user through the injection device insertion, the injection process and injection device replacement and to provide reminders as to when the scheduled time for the next injection is due. The processor 25 also causes a dosing history to be stored in the memory of the supplementary device 2 and optionally transmitted via the wireless unit 28.

Figure 9:
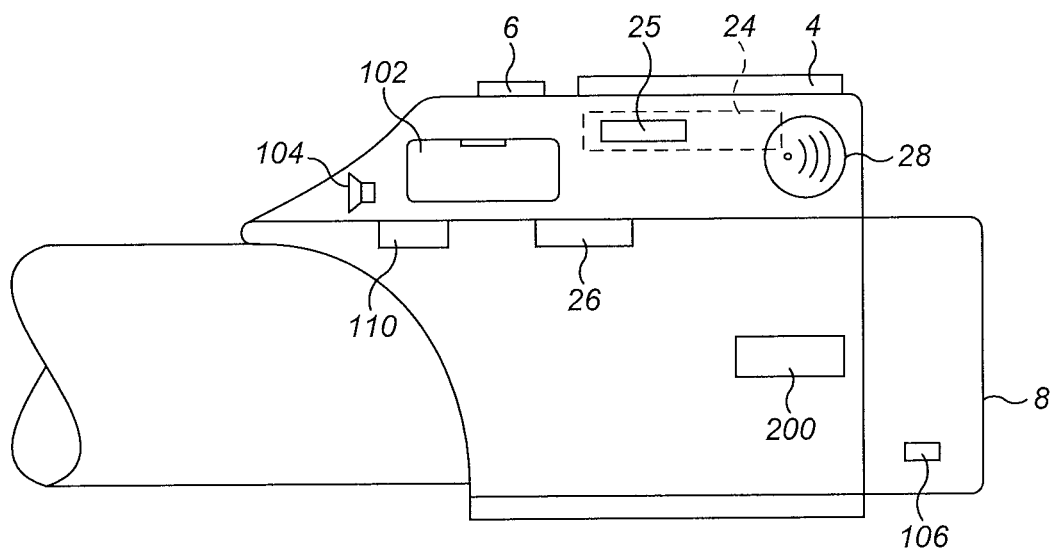
FIG. 9 shows a side view of another embodiment of the supplementary device of FIGS. 2a and 2b and an attached injection device and illustrates some of the major internal and external components of the supplementary device.

FIG. 9 illustrates some of the major internal and external components of the supplementary device 2 according to some other embodiments of the disclosure. The supplementary device 2 of these embodiments is suitable for use with the sleeve activated injection device 10 shown in FIGS. 1C and 1D.

The supplementary device 2 shown in FIG. 9 contains many of the same components as described with reference to FIG. 3. These components serve the same function and are not described in detail again. The first non-contact status sensor 110 of FIG. 9 may be a Hall sensor, an inductive sensor or an AMR sensor. The first non-contact status sensor 110 may also comprise a permanent magnet or an electromagnet. The second non-contact status sensor 200 of FIG. 9 may be a Hall sensor, an inductive sensor or an AMR sensor. The second non-contact status sensor 200 may also comprise a permanent magnet or an electromagnet.

In all of the embodiments described herein, the first and second sensors (110, 200) are referred to as non-contact sensors. However, they may each also be termed "proximity sensors", or "inductive proximity sensors" as each of the sensors is configured to have a current or signal induced in it. In contrast, an optical sensing system requires active monitoring by an image capture device, correct illumination conditions and image analysis software. Having sensors in which the movement of a particular component of the injection device 10 induces a signal in the sensor provides a less power intensive method of non-contact sensing.

In the supplementary device 2 of FIG. 9, the second non-contact status sensor 200 is configured to detect the movement of a different type of moveable component than in the device shown in FIG. 3. Therefore, the second non-contact status sensor 200 is located adjacent the cylindrical part of the housing 11 of the injection device 10.

Further details of the injection device 10 of FIGS. 1C and 1D and the supplementary device 2 of FIG. 9 will now be discussed with reference to FIGS. 10 to 14.

Figure 10:
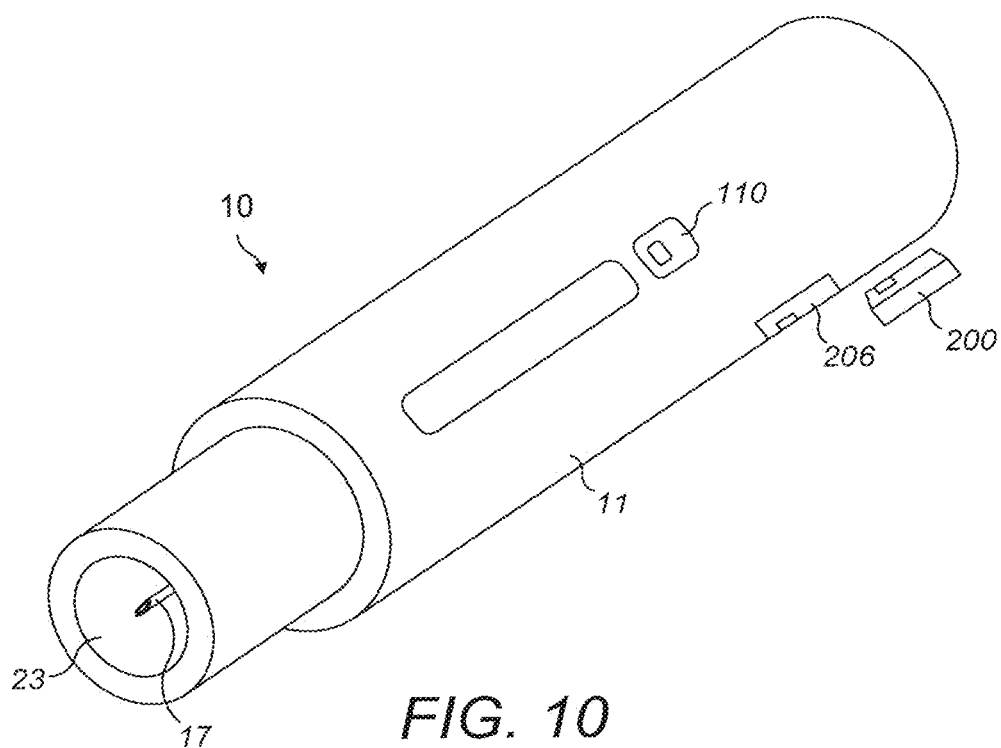
FIG. 10 is a perspective view of the injection device of FIGS. 1C and 1D and illustrates schematically the position of first and second non-contact sensors.
Figure 11:
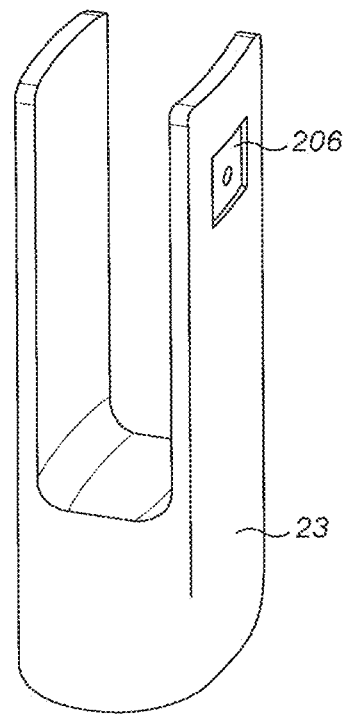
FIG. 11 shows a sleeve of the injection device of FIGS. 1C and 1D.

FIG. 10 is a perspective view of the injection device 10 of FIGS. 1C and 1D and also illustrates schematically the first and second non-contact sensors. FIG. 11 shows the sleeve 23. FIG. 10 shows the injection device 10 in a pre-activation state. The needle 17 is shielded by the sleeve 23. As shown in FIG. 11, the sleeve 23 comprises a magnetic section 206 (also referred to herein as a sleeve segment or a sleeve sensor segment). The magnetic section 206 may be inlaid into the sleeve 23 or stamped or printed onto the surface of the sleeve 23. The magnetic section 206 is located at or near the distal end of the sleeve 23, as shown in FIG. 11. The magnetic section 206 may be for example a metal plate magnet or a magnetized plastic material. Alternatively, the magnetic section 206 may be replaced with a metal part having a high magnetic permeability.

The approximate position of the magnetic section 206 within the injection device 10 is shown in FIG. 10. The magnetic section 206 is positioned on the outer surface of the sleeve 23 so as to be as close to the housing 11 of the injection device 10 as possible. The approximate position of the second non-contact status sensor 200 when the supplementary device 2 is attached to the injection device 10 is also shown. The second non-contact status sensor 200 may be located close to the distal end of the injection device 10. In the pre-activation configuration, the magnetic section 206 is not located underneath the second non-contact status sensor 200.

The approximate position of the first non-contact status sensor 110 is also shown. In some particular embodiments, the first non-contact status sensor 110 may be located closer to the proximal end of the supplementary device 2 than the second sensor and may be offset from the second sensor by approximately 90 degrees. This may help to prevent interference between the two sensors and the magnetic segments they detect.

Figure 12:
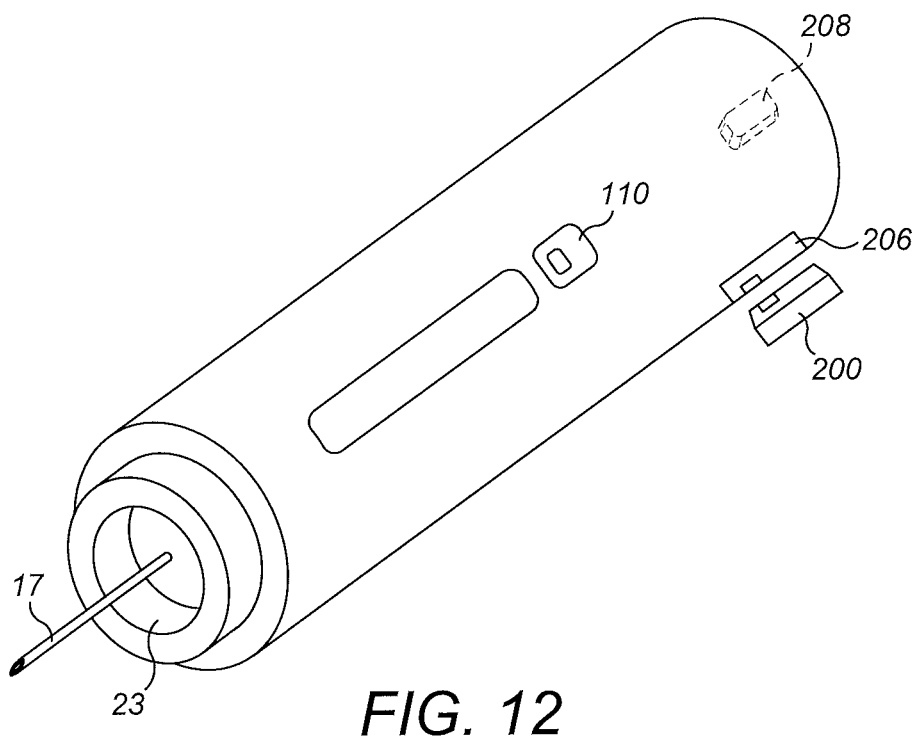
FIG. 12 is a perspective view of the injection device of FIGS. 1C and 1D and illustrates schematically the position of components in a post-activation and pre-ejection state.

FIG. 12 illustrates the position of the components described above after the sleeve 23 has been activated. The sleeve 23 is activated by depressing it into the main body 11 of the injection device 10. If the user has the injection device 10 positioned against their skin, then this causes injection of the needle 17 into the user. However, injection of the user is not necessary for the injection device 10 and supplementary device 2 to perform their functions. The term "ejection" is used throughout this specification to indicate that the injection device 10 will perform its functions (i.e., will eject medicament) irrespective of whether a user has injected themselves.

FIG. 12 illustrates the moment at which the sleeve 23 has been activated and the ejection is about to commence. Thus, the injection device 10 may be described as being in a post-activation state, but also in a pre-ejection state. The sleeve 23 has moved distally within the injection device 10. The magnetic section 206 has therefore also moved distally and is now located underneath the second non-contact status sensor 200.

In some embodiments, the second non-contact status sensor 200 is a Hall sensor, and the movement of the magnetic section 206 induces a signal in the sensor. The processor 25 detects this signal and can infer that the injection device 10 has been activated. The processor 25 may then control the display 4 accordingly (see FIGS. 15-16).

Figure 13:
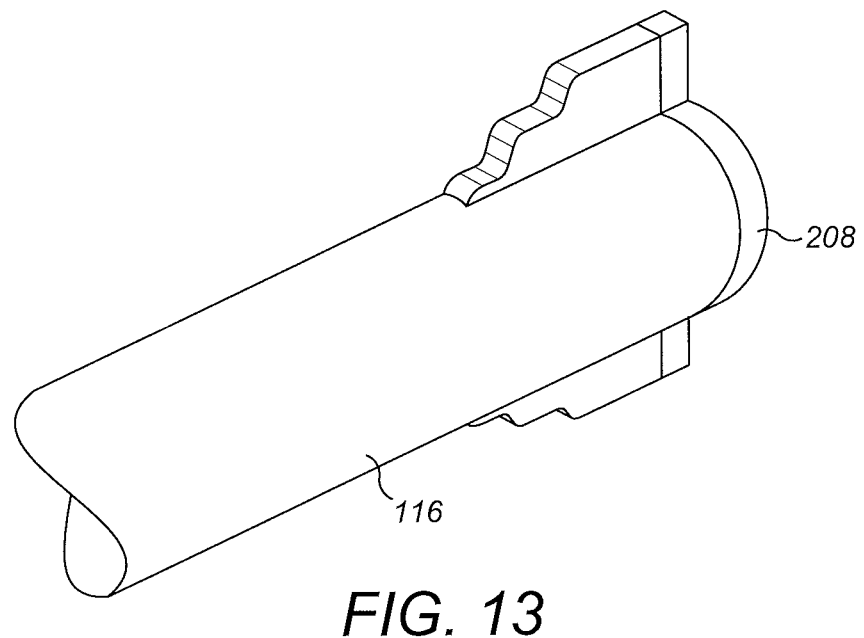
FIG. 13 shows a plunger of the injection device of FIGS. 1C and 1D.

As shown in detail in FIG. 13, the plunger 116 of the injection device 10 may have an additional part 208 at its distal end. This may be referred to as the plunger section 208 or second magnetic section 208. The plunger section 208 may be for example a metal plate magnet or a magnetized plastic material. Alternatively, the plunger section 208 may be replaced with a metal part having a high magnetic permeability. The approximate position of the plunger section 208 within the injection device 10 in the pre-ejection configuration is indicated in FIG. 12.

Figure 14:
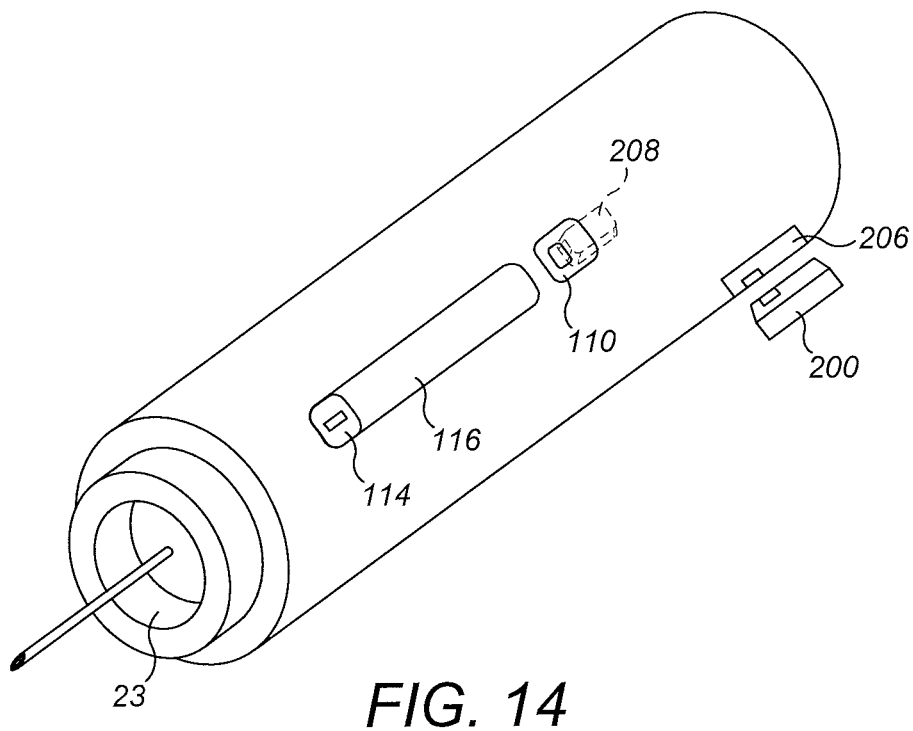
FIG. 14 is a perspective view of the injection device of FIGS. 1C and 1D and illustrates schematically the position of components in a post-ejection state.

After the injection device 10 has been activated, the plunger 116 begins to move proximally and to cause the medicament to be ejected. The plunger 116 continues to move until it reaches its final position, as shown in FIG. 14. FIG. 14 therefore shows the injection device 10 in a post-ejection configuration. In this configuration, the plunger section 208 has moved underneath the first non-contact status sensor 110 which causes a signal to be induced in the first non-contact status sensor 110. The processor detects this signal and can infer that the ejection process has been fully completed. The processor 25 may then control the display 4 accordingly, for example to begin indication of a "dwell time".

Figure 15:
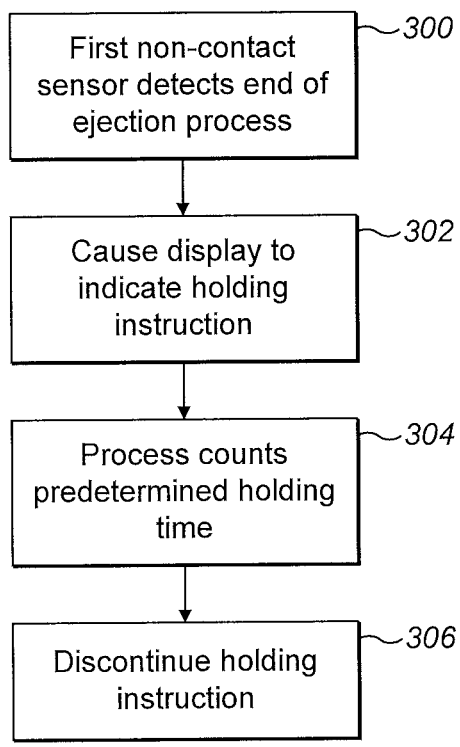
FIG. 15 is a flow chart showing operations of a supplementary device according to some embodiments of the disclosure.

FIG. 15 is a flow chart showing operations of the supplementary device 2 according to some embodiments of the disclosure. These operations are applicable to all of the embodiments of the supplementary device 2 described above. The operation begins at step 300 in which the first non-contact sensor 110 detects that the ejection process has ended. The processor 25 may receive signals from the first non-contact sensor 110 in order to make the determination. The first non-contact sensor 110 may take a number of forms as described above. In the simplest embodiments of the disclosure, the first non-contact sensor 110 may be the only sensor in the supplementary device 2 configured to monitor the attached injection device 10 (i.e., the second non-contact status sensor 200 may not be present). The determination that the ejection process has finished may be the first determination about the injection device 10 made by the processor 25.

Upon determining that the ejection process has ended, at step 302 the processor 25 controls the display unit 4 to show a holding instruction. This instruction can take a number of forms, for example the words "Hold" or "Wait and Hold" may be displayed. Any other suitable words conveying the same meaning may take the place of these. Alternatively, or in addition to the words, the display may show an image or an animation to indicate that the user should leave the injection device 10 injected into their skin. The image or animation may be of any suitable form, for example a timer which counts up or down or a graphic which gets larger/smaller or which fills or un-fills. This holding instruction may help to ensure that the user observes the correct dwell time.

At step 304 the processor counts a predetermined holding time. This holding time allows the injected medicament to be diffused away from the injection site by action of the user's blood flow. A typical holding time may be between 5-10 seconds. Measurement of the holding time (step 304) may begin simultaneously with step 302. The internal counting of the holding time by the processor 25 may optionally be accompanied by audible feedback produced by the audio module 104. The audible feedback may take any suitable form, such as a spoken countdown (e.g., 5, 4, 3, 2, 1) or a series of pips.

At step 306, once the predetermined holding time is complete, the processor 25 controls the display unit 4 to discontinue the holding instruction. The holding instruction may be replaced with a confirmation that the injection is complete and/or an indication that the user can now remove the injection device 10.

Figure 16A:
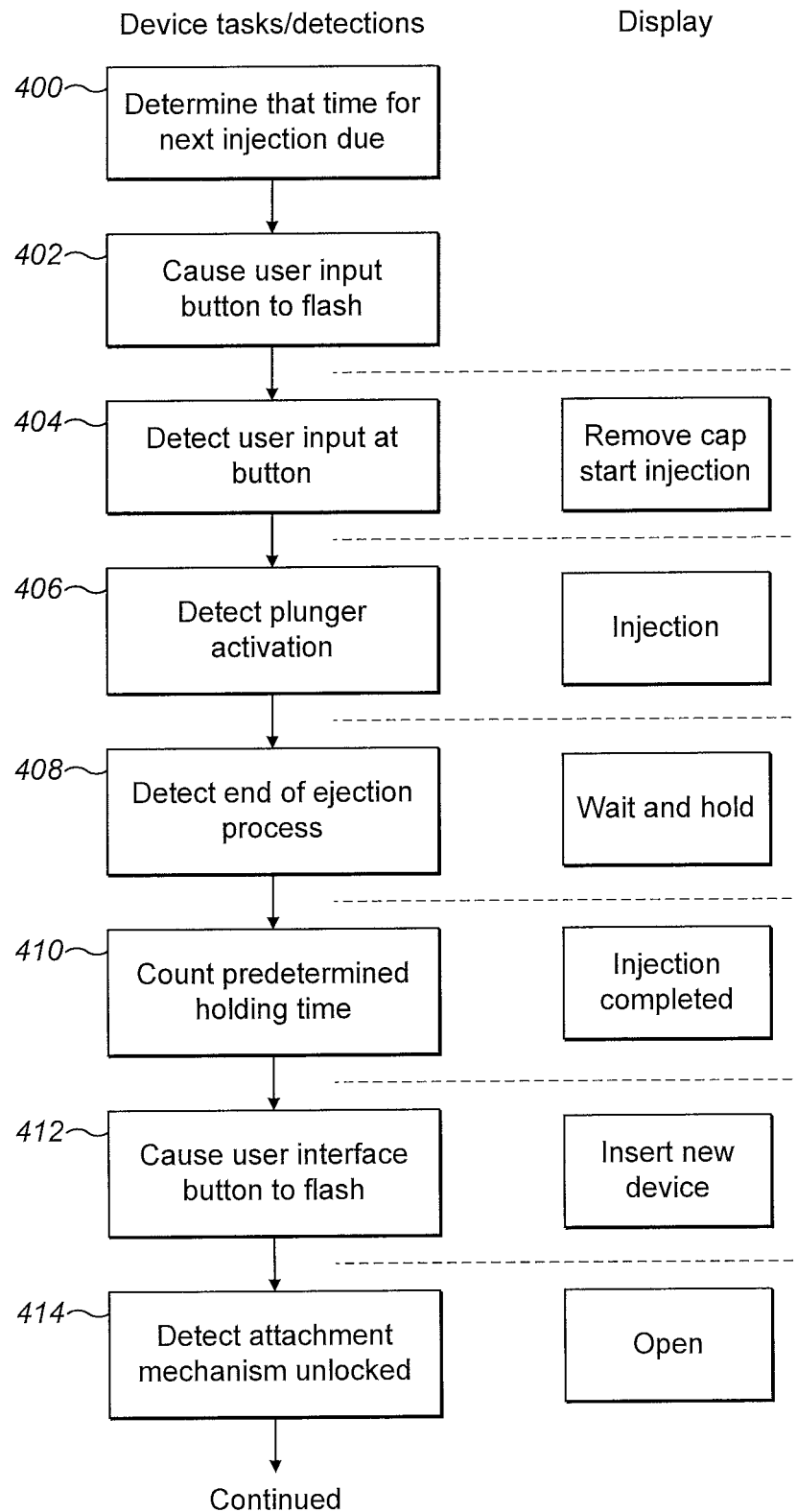
FIGS. 16a and 16b are a flowchart illustrating optional additional operations which can be performed by the supplementary device and exemplary wording to be displayed on a display of the supplementary device.
Figure 16B:
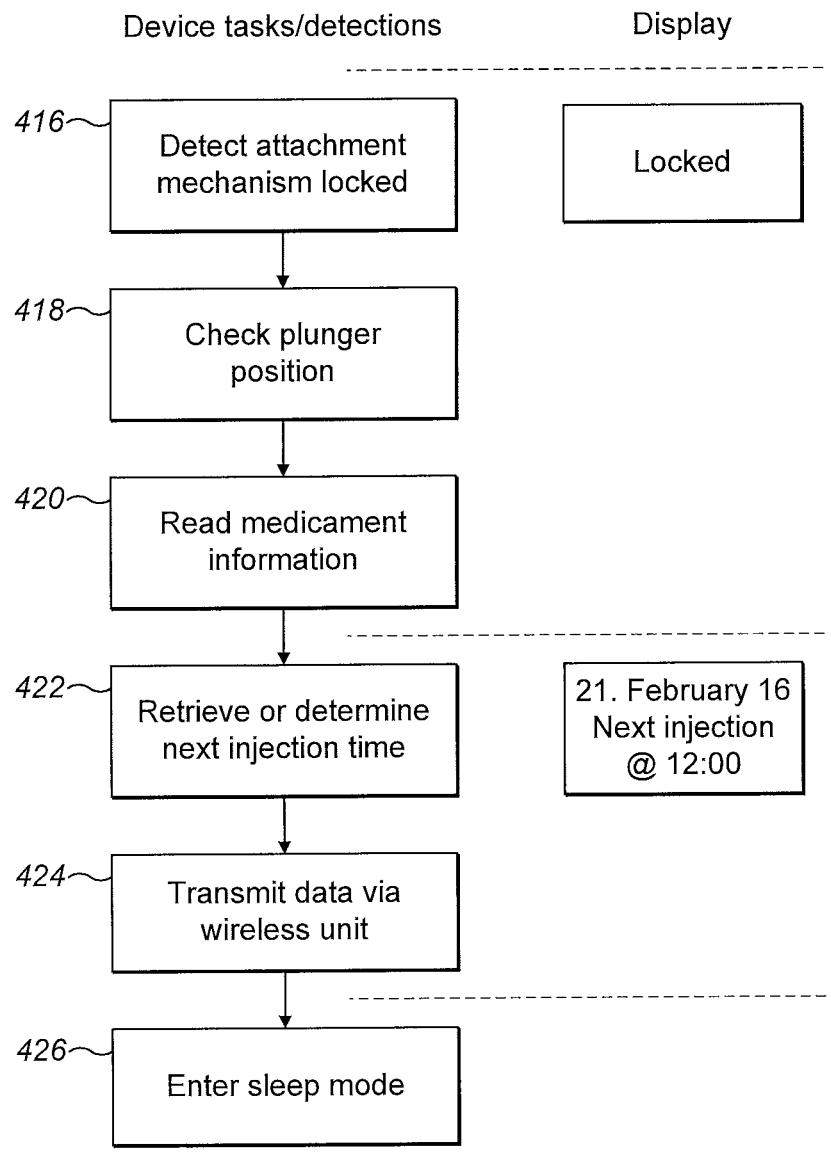

FIGS. 16a and 16b show a flow chart illustrating optional additional operations which can be performed by the supplementary device 2 and exemplary wording to be displayed on the display 4 during the various operational stages. These operations are applicable to all of the embodiments of the supplementary device 2 described above. FIG. 16b is a continuation of FIG. 16a.

At step 400, the supplementary device 2 (with an attached injection device 10) determines that the time of the user's next scheduled injection is due. At this time the display 4 is deactivated and the supplementary device 2 may also be in 'sleep mode'. The electronics 24 may store at least the time and date of the user's next scheduled injection in the memory and the supplementary device 2 may be programmed to wake up form sleep mode at this time. At step 402, in response to determining that the time of the user's next scheduled injection is due, the processor 25 causes the user input 6 to flash, alternate its color or otherwise change its appearance in order to become more noticeable. In some other embodiments, the processor 25 may instead or in addition causes another light emitting part of the supplementary device 2 to change its appearance, such as one or more dedicated LEDs (not shown) or by activating and using the display 4. For example, the display 4 may display the words "Next Injection Due" or similar.

At step 404, the supplementary device 2 detects an input at the user input 6. The user input may be a button press or touch input at the user input 6. After receiving the user input, the supplementary device 2 activates the display 4, if not already active. The display 4 is controlled to show the words "Remove Cap" and "Start Injection", either simultaneously or sequentially. Alternatively or in addition the display 4 may show one or more images or animations illustrating removal of the outer needle cap 12, inserting the needle 17 into a user and beginning of medicament injection.

At step 406, the second non-contact sensor 200 detects activation of the injection device 10 ejection process by sensing movement of the plunger 116, as described above with reference to FIGS. 8a to 8c. Once movement of the plunger 116 has been detected, the display 4 may show the words "Injection" or "Injection in Progress" or similar.

At step 408, the first non-contact sensor 110 detects the end of the ejection process. The processor 25 may receive signals from the first non-contact sensor 110 in order to make the determination. The first non-contact sensor 110 may take a number of forms as described above with reference to FIGS. 4a to 7b.

Upon determining that the ejection process has ended, the processor 25 controls the display unit 4 to show a holding instruction. For example, the words "Hold" or "Wait and Hold" may be displayed. Any other suitable words conveying the same meaning may take the place of these. Alternatively, or in addition to the words, the display may show an image or an animation to indicate that the user should leave the injection device 10 injected into their skin.

At step 410 the processor 25 counts a predetermined holding time. This holding time allows the injected medicament to be diffused away from the injection site by action of the user's blood flow. A typical holding time may be between 5-10 seconds. Measurement of the holding time (step 410) may begin simultaneously with step 408. The internal counting of the holding time by the processor 25 may optionally be accompanied by audible feedback produced by the audio module 104. The audible feedback may take any suitable form, such as a spoken countdown (e.g. 5, 4, 3, 2, 1) or a series of pips.

At step 412, after a further predetermined time, the supplementary device 2 causes the user input 6 to flash, alternate its color or otherwise change its appearance in order to become more noticeable. The appearance of the user input 6 at this stage may be the same as in step 402, or maybe different. For example, the user input 6 could flash a green color in step 402 to indicate that the injection device 10 is ready to use and could flash a red color in step 412 to indicate that the injection device 10 is empty and needs replacing. In some other embodiments, the processor 25 may instead or in addition causes another light emitting part of the supplementary device 2 to change its appearance, such as one or more dedicated LEDs (not shown). At this time, the display 4 may be controlled to show the words "Insert New Device", "Change Device" or similar. This may be replaced or augmented with an image or animation showing a new injection device 10 being inserted into the supplementary device 2.

At step 414, the locking sensor 106 of the supplementary device 2 detects that the attachment mechanism 8 has been unlocked. The processor 25 may receive signals from the locking sensor 106 in order to make this detection. The display 4 may be controlled to show the word "Open" or otherwise to indicate that no device is attached. Alternatively, the display 4 may be controlled to continue showing the words "Change Device" or similar, as shown in FIG. 2b.

The user then inserts a new injection device 10 into the supplementary device 2 and locks the attachment mechanism 8. At step 416 the locking sensor 106 of the supplementary device 2 detects that the attachment mechanism 8 has been locked. The display 4 may be controlled to show the word "Locked" or otherwise to indicate that a new device has been attached. The supplementary device 2 may then execute a plausibility check on the new injection device 10. At step 418, the second non-contact status sensor 200 checks the position of the plunger 116 to make sure that the newly inserted injection device is in a pre-activation configuration. If the second non-contact status sensor 200 detects that the newly inserted injection device 10 has already been used, a warning or error message may be displayed on display 4. For example, the words "Injector already used" or similar may be displayed. If it can be inferred from the signals output by the second non-contact status sensor 200 that a mechanical fault has occurred, such as that the injection device 10 was incorrectly assembled or does not contain the correct amount of medicament, suitable alarm signals and information may be generated and displayed by the supplementary device 2. This may help in preventing an accidental under-dose. At step 420, the optical sensor 26, if present, may be used to read to information 100 printed on the injection device 10. This allows the supplementary device 2 to determine that the user has inserted an injection device 10 containing the correct medicament, or the correct amount of medicament. If it is determined that the newly inserted injection device 10 contains the wrong medicament, suitable alarm signals and information may be generated and displayed by the supplementary device 2.

At step 422, if the plausibility checks are passed, the processor 25 retrieves or determines the time and date of the user's next scheduled injection. At least the next scheduled injection information may be stored in the memory of the supplementary device 2 and retrieved from there by the processor 25. The display 4 is then controlled to display this information.

Alternatively, the supplementary device 2 may be programmed to calculate the time of the next dose using stored or retrieved information relating to the user, e.g. physiological information. In addition, the time at which the user should perform the next injection may depend on the amount of medicament previously injected and the frequency of the previous injections. If no such information is stored, the supplementary device 2 may be programmed to retrieve the information from an external device using wireless unit 28. In a particular example, the external device may be a blood glucose meter, or a computer which stores the readings taken by a blood glucose meter. This arrangement allows the timing of the user's injections to be updated as a result of the user's blood glucose readings and communicated to the user automatically.

At step 424 the supplementary device 2 transmits data relating to the recently performed injection process to an external device via the wireless unit 28. The information may contain both the type and amount of medicament injected and the exact time of administration. The processor 25 of the supplementary device 2 has an internal clock in order to create time stamps associated with the injection events. The clock may be a relative clock or an absolute clock. The external device may provide an absolute time. The external device may be a computer or smart phone running an app. The user or the user's healthcare professional may view and manage their dosage regime and the user's adherence to the regime using the external device or app.

After transmitting the data or after the information regarding the user's next scheduled injection has been displayed for a predetermined period of time, the supplementary device 2 enters sleep mode and the display 4 is deactivated. The process may then begin again at step 400.

The supplementary device 2 may be pre-programmed with information relating to the frequency at which the user should perform injections. This programming may take the form of a maximum time between injections or a medical regimen associated with the user of the supplementary device 2. For example, the supplementary device 2 may be pre-programmed with information specifying that the maximum time between injections should be 24 hours. In some other embodiments, the medical regimen may be more detailed, such as to specify specific times of day at which the user is to perform an injection operation using the injection device 10.

Optionally, when the supplementary device 2 determines that it is time for the user to perform a subsequent injection, it causes a reminder signal to be sent via the wireless unit 28 to the associated external device. The external device may then notify and remind the user that their next injection is due. This is advantageous as the user may not wish to carry the injection device 10 and/or supplementary device 2 with them, but may in any case by carrying a smart phone or similar device. Thus the user can be reminded of the need for a subsequent injection via a separate device which they carry with them. Furthermore, the injection device 10 may need to be kept under specific conditions, such as in a refrigerator or a freezer, such that it is not possible for a user to carry the injection device with them. It is therefore easy for a user to forget about the times at which an injection needs to be performed.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl- LysB28ProB29 human insulin; B30-N-myristoyl- ThrB29LysB30 human insulin; B30-N-palmitoyl- ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immuno-pharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (such as, for example, adjustments, additions, or removals) of various components of the substances, formulations, apparatuses, methods, systems, devices, and embodiments described herein may be made without departing from the full scope and spirit of the present inventive concepts, which encompass such modifications and any equivalents thereof.

The invention claimed is:

1. A supplementary device configured to be releasably attached to a drug delivery device comprising a first moveable component comprising a resilient member configured to change position between a first configuration when the drug delivery device is in a pre-ejection state and a second configuration when the drug delivery device is in a post-ejection state, the supplementary device comprising:
   a first non-contact sensor configured to output signals indicative of a position of the first moveable component within the drug delivery device when the resilient member changes position from the first configuration to the second configuration; and
   a processor configured to:
      receive the signals output from the first non-contact sensor;
      determine based on the signals a moment at which the resilient member changes position from the first configuration to the second configuration and the drug delivery device changes from a pre-ejection state to a post-ejection state; and
      in response to determining that the drug delivery device has changed from the pre-ejection state to the post-ejection state, cause a display of the supplementary device to visually indicate that a user should hold the drug delivery device in its current position for a predetermined period of time, wherein the first non-contact sensor is a Hall effect, inductive, piezoelectric, or anisotropic magnetoresistive sensor.

2. The supplementary device according to claim 1, the first moveable component comprising a ferromagnetic material, wherein the first non-contact sensor is a Hall effect sensor or an anisotropic magnetoresistive sensor; and the Hall effect sensor or anisotropic magnetoresistive sensor is configured to output signals indicative of a position of the first moveable component.

3. The supplementary device according to claim 1, wherein the first non-contact sensor is an inductive sensor or a piezoelectric sensor.

4. The supplementary device according to claim 1, wherein the supplementary device further comprises a second non-contact sensor configured to output signals indicative of the position of a second moveable component within the drug delivery device.

5. The supplementary device according to claim 4, the second moveable component of the drug delivery device comprising a magnet, wherein the second non-contact sensor is a Hall effect sensor configured to output signals indicative of a position of the magnet of the second component.

6. The supplementary device according to claim 4, wherein the second non-contact sensor is an anisotropic magnetoresistive sensor.

7. The supplementary device according to claim 1, further comprising a wireless unit configured to transmit data to at least one external device.

8. The supplementary device according to claim 1, wherein the supplementary device is configured to determine a time at which a next medicament dose is due.

9. The supplementary device according to claim 8, further comprising a light emitting user input configured to change appearance at a time at which the next medicament dose is due.

10. The supplementary device according to claim 1, further comprising an audio module, wherein the processor is configured to cause the audio module to produce an audible indication at the same time the display visually indicates that the user should hold the drug delivery device in its current position for the predetermined period of time.

* * * * *